United States Patent
Dewey

(10) Patent No.: US 11,911,282 B2
(45) Date of Patent: Feb. 27, 2024

(54) SPINAL IMPLANT SYSTEM AND METHOD

(71) Applicant: WARSAW ORTHOPEDIC INC., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 424 days.

(21) Appl. No.: 17/166,172

(22) Filed: Feb. 3, 2021

(65) Prior Publication Data

US 2021/0330470 A1 Oct. 28, 2021

Related U.S. Application Data

(60) Provisional application No. 63/014,863, filed on Apr. 24, 2020.

(51) Int. Cl.
*A61F 2/44* (2006.01)
*A61F 2/30* (2006.01)

(52) U.S. Cl.
CPC .... *A61F 2/4425* (2013.01); *A61F 2002/3093* (2013.01)

(58) Field of Classification Search
CPC ................................ A61F 2/4455; A61F 2/446
See application file for complete search history.

(56) References Cited

U.S. PATENT DOCUMENTS

| | | | | |
|---|---|---|---|---|
| 6,752,832 B2* | 6/2004 | Neumann | ............. | A61F 2/4611 606/247 |
| 7,674,296 B2* | 3/2010 | Rhoda | ..................... | A61F 2/442 623/17.11 |
| 7,758,648 B2* | 7/2010 | Castleman | ............ | A61F 2/4611 623/17.11 |
| 8,192,495 B2* | 6/2012 | Simpson | ................. | A61F 2/442 623/17.15 |
| 8,771,360 B2* | 7/2014 | Jimenez | ................ | A61F 2/4611 623/17.16 |
| 11,497,622 B2* | 11/2022 | Jimenez | ................... | A61F 2/447 |
| 2007/0191954 A1* | 8/2007 | Hansell | ................. | A61F 2/4611 623/17.15 |
| 2007/0198089 A1* | 8/2007 | Moskowitz | ............. | A61F 2/442 623/17.11 |
| 2007/0222100 A1* | 9/2007 | Husted | ..................... | B27N 3/08 264/408 |
| 2007/0255415 A1* | 11/2007 | Edie | ...................... | A61F 2/4611 606/90 |

(Continued)

*Primary Examiner* — Ellen C Hammond
(74) *Attorney, Agent, or Firm* — Sorell, Lenna & Schmidt, LLP

(57) ABSTRACT

A spinal implant includes an outer body extending along an axis between opposite first and second ends. The outer body defines a bore and a first thread. An inner shaft includes opposite first and second ends. The second end of the inner shaft is positioned in the bore. The inner shaft includes a second thread that mates with the first thread. The second thread includes a series of gear teeth. An end plate is coupled to the first end of the inner shaft. A driver includes a gear configured to engage the gear teeth such that rotation of the driver relative to the outer body rotates the inner shaft relative to the outer body to translate the inner shaft relative to the outer body along the longitudinal axis. Systems and methods are disclosed.

20 Claims, 13 Drawing Sheets

(56) References Cited

U.S. PATENT DOCUMENTS

| | | | |
|---|---|---|---|
| 2008/0210039 A1* | 9/2008 | Brun | F16H 25/229 74/424.94 |
| 2009/0164017 A1* | 6/2009 | Sommerich | A61F 2/44 623/17.16 |
| 2009/0210061 A1* | 8/2009 | Sledge | A61F 2/4465 623/17.11 |
| 2011/0054616 A1* | 3/2011 | Kamran | A61F 2/4465 623/17.11 |
| 2011/0138948 A1* | 6/2011 | Jimenez | A61F 2/4611 74/424.82 |
| 2014/0277506 A1* | 9/2014 | Hadden, Jr. | A61F 2/44 623/17.16 |
| 2015/0005880 A1* | 1/2015 | Popa | A61F 2/446 623/17.13 |
| 2015/0025633 A1* | 1/2015 | McLaughlin | A61F 2/4455 623/17.15 |
| 2016/0100955 A1* | 4/2016 | Stinchfield | A61F 2/4465 623/17.15 |
| 2017/0319350 A1* | 11/2017 | McLaughlin | A61F 2/4611 |
| 2019/0000645 A1* | 1/2019 | Stinchfield | A61F 2/4465 |
| 2021/0330470 A1* | 10/2021 | Dewey | A61F 2/446 |
| 2021/0330471 A1* | 10/2021 | Dewey | A61F 2/446 |
| 2023/0013150 A1* | 1/2023 | Stinchfield | A61F 2/44 |

* cited by examiner

SPINAL IMPLANT SYSTEM AND METHOD

TECHNICAL FIELD

The present disclosure generally relates to medical devices for the treatment of musculoskeletal disorders, and more particularly to a spinal construct configured for disposal with spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae.

Furthermore, it is noted that there is an increasing need for polyetheretherketone (PEEK) based expandable corpectomy devices. However, since PEEK is weaker than other materials, such as, for example, titanium or stainless steel, PEEK based expandable corpectomy devices tend to break under high load scenarios, such as, for example, when the devices bear anatomical loads. This disclosure describes an improvement over these prior technologies.

SUMMARY

In one embodiment, a spinal implant is provided. The spinal implant includes an outer body extending along a longitudinal axis between opposite first and second ends. The outer body comprises an inner surface. The inner surface defines a bore and a first thread. An inner shaft comprises opposite first and second ends. The second end of the inner shaft is positioned in the bore. The inner shaft comprises an outer surface defining a second thread that mates with the first thread. The second thread comprises a series of gear teeth. An end plate is coupled to the first end of the inner shaft. A driver comprises a gear configured to engage the gear teeth such that rotation of the driver relative to the outer body rotates the inner shaft relative to the outer body to translate the inner shaft relative to the outer body along the longitudinal axis.

In one embodiment, a spinal implant is provided. The spinal implant includes an outer body extending along a first longitudinal axis between opposite first and second ends. The outer body comprises an inner surface. The inner surface defines a bore and a first thread. The outer body is linear along the first longitudinal axis from the first end of the outer body to the second end of the outer body. A hollow inner shaft extends along a second longitudinal axis between opposite first and second ends. The second end of the inner shaft is positioned in the bore. The inner shaft comprises an outer surface defining a second thread that mates with the first thread. The second thread comprises a series of gear teeth. A first end plate is coupled to the first end of the inner shaft. The first end plate defines a third longitudinal axis. A second end plate is coupled to the second end of the outer body. The second end plate defines a fourth longitudinal axis that extends perpendicular to the first longitudinal axis. A driver comprises a gear configured to engage the gear teeth such that rotation of the driver relative to the outer body rotates the inner shaft relative to the outer body to translate the inner shaft relative to the outer body along the first longitudinal axis. The fourth longitudinal axis is parallel to the third longitudinal axis as the inner shaft translates relative to the outer body along the first longitudinal axis. The inner shaft comprises a plurality of tiers, the tiers defining the second thread, the tiers being fixed relative to one another as the inner shaft translates relative to the outer body along the first longitudinal axis.

In one embodiment, a spinal implant is provided. The spinal implant includes an outer body extending along a first longitudinal axis between opposite first and second ends. The outer body comprises an inner surface. The inner surface defines a bore and a first thread. The outer body is curved along the first longitudinal axis. A hollow inner shaft extends along a second longitudinal axis between opposite first and second ends. The second end of the inner shaft is positioned in the bore. The inner shaft comprises an outer surface defining a second thread that mates with the first thread. The second thread comprises a series of gear teeth. A first end plate is coupled to the first end of the inner shaft. The first end plate defines a third longitudinal axis. A second end plate is coupled to the second end of the outer body. The second end plate defines a fourth longitudinal axis that extends perpendicular to the first longitudinal axis. A driver comprises a gear configured to engage the gear teeth such that rotation of the driver relative to the outer body rotates the inner shaft relative to the outer body to translate the inner shaft relative to the outer body along the first longitudinal axis. The fourth longitudinal axis extends at an acute angle relative to the third longitudinal axis as the inner shaft translates relative to the outer body along the first longitudinal axis. The inner shaft comprises a plurality of tiers. The tiers define the second thread. The tiers move relative to one another such that the inner shaft bends along the second longitudinal axis as the inner shaft translates relative to the outer body along the first longitudinal axis such that the inner shaft bends along the second longitudinal axis.

BRIEF DESCRIPTION OF THE DRAWINGS

The present disclosure will become more readily apparent from the specific description accompanied by the following drawings, in which.

DETAILED DESCRIPTION

Figure 1:
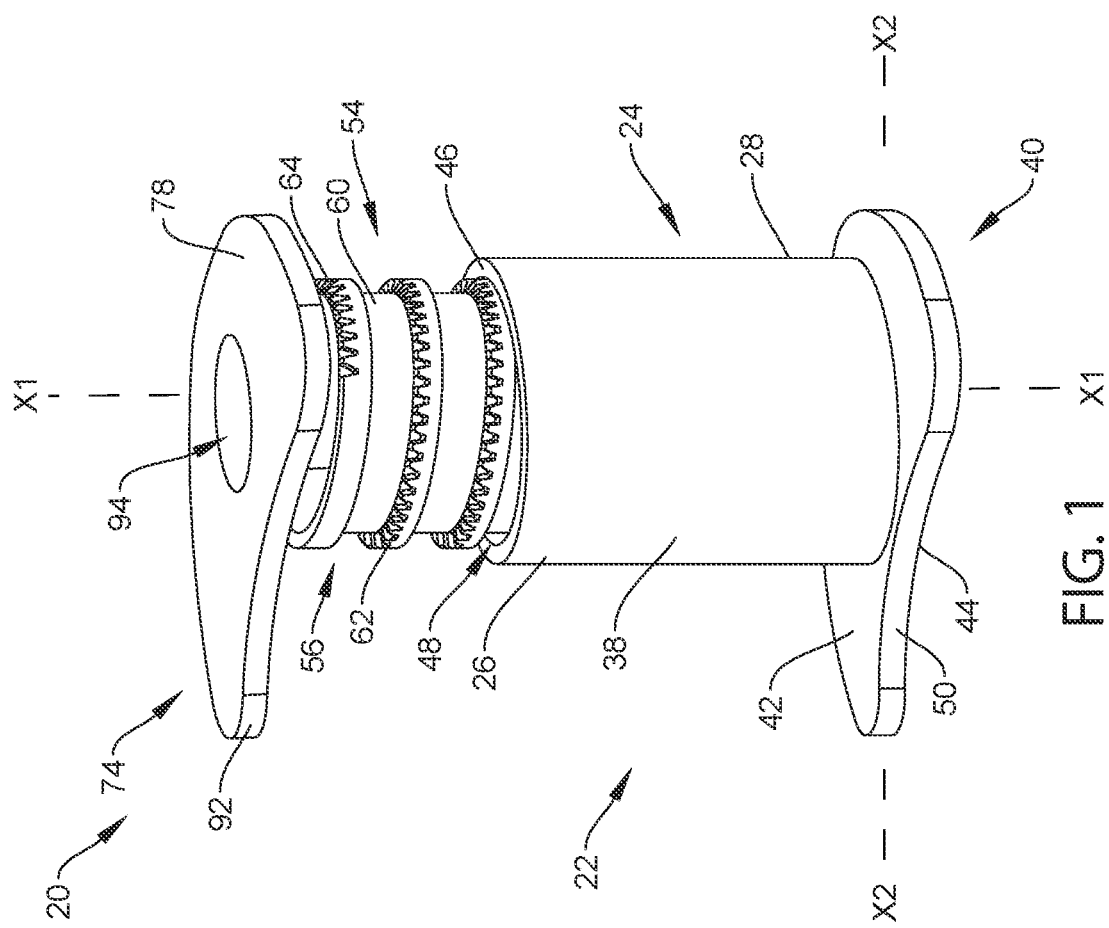
FIG. 1 is a perspective view of components of one embodiment of a spinal implant system in accordance with the principles of the present disclosure.
Figure 2:
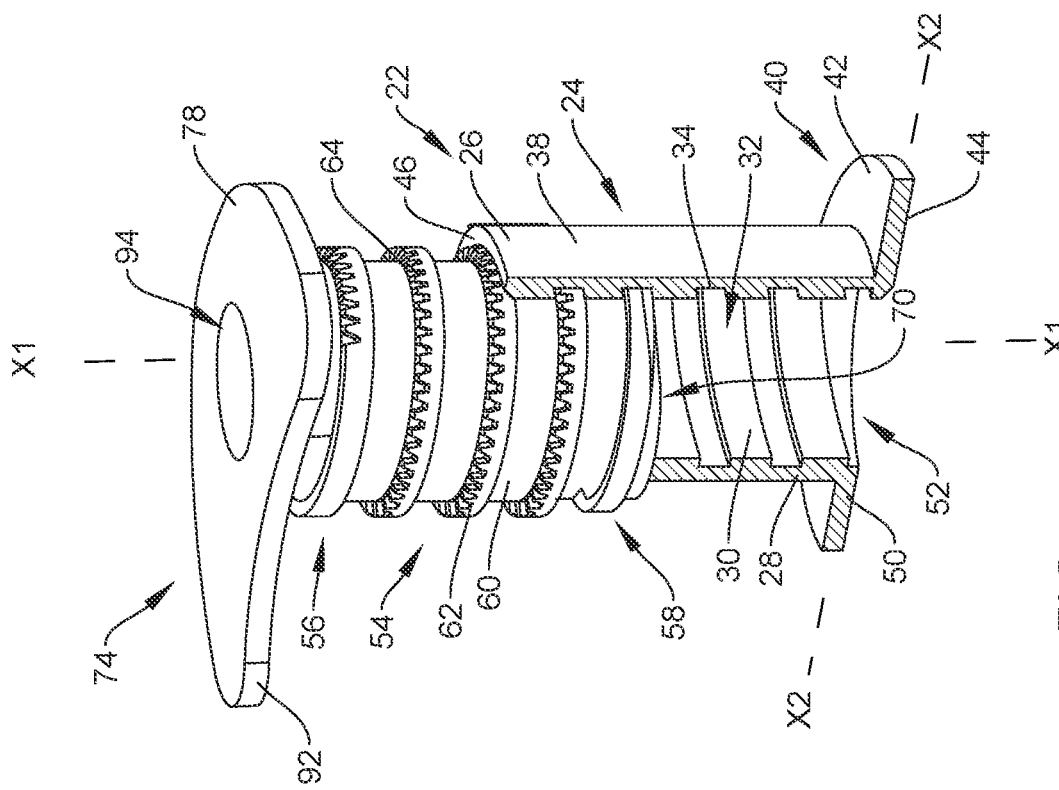
FIG. 2 is a perspective view, in part cross-section, of components of the system shown in FIG. 1.
Figure 3:
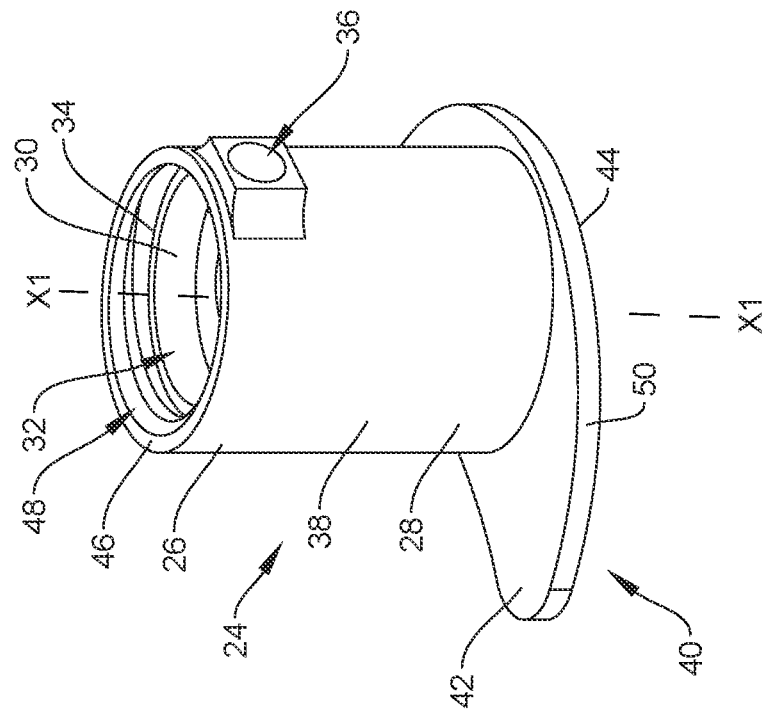
FIG. 3 is a perspective view of a component of the system shown in FIG. 1.
Figure 4:
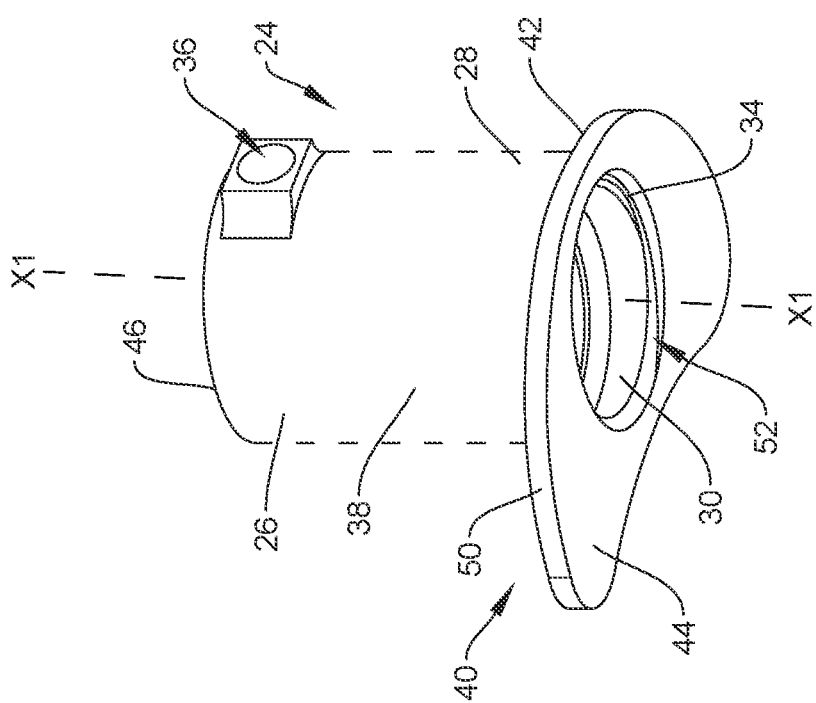
FIG. 4 is a perspective view of a component of the system shown in FIG. 1.

The exemplary embodiments of a surgical system and related methods of use disclosed are discussed in terms of medical devices for the treatment of musculoskeletal disorders and more particularly, in terms of a spinal implant system that includes an expandable interbody implant configured for disposal with spaced vertebrae and a method for treating a spine.

In some embodiments, the spinal implant system includes a PEEK based expandable corpectomy implant that overcomes the deficiencies of other PEEK based expandable corpectomy devices by providing a threaded cage in which threads allow large amounts of surface area (across multiple threads) for bearing loads.

In some embodiments, the spinal implant system includes the expandable implant includes an outer body, an inner shaft, a superior end plate and a geared driver.

In some embodiments, the outer body is provided with a threaded inner bore and a port for accessing the inner bore. In some embodiments, the outer body includes an end plate attached for engaging the end plate of an inferior vertebral body. In some embodiments, the end plate is cannulated. In some embodiments, the end plate is perforated. In some embodiments, the end plate is solid.

In some embodiments, the inner shaft is provided with an external thread shaped to mate with the internal thread of the outer body. Superimposed onto the external thread is a series of gear teeth. In some embodiments, the inner shaft is hollow to allow bone growth. In some embodiments, the inner shaft includes a lumen configured for disposal of bone graft material. In some embodiments, the lumen is perforated to allow bone growth into the lumen. In some embodiments, the gear teeth are straight cut gear teeth. However, it is envisioned that the gear teeth may include other designs, such as, for example, a bevel gear or a helical gear pattern.

In some embodiments, the superior end plate acts as an interference between the inner shaft and a superior vertebral body. For example, the superior end plate may be axially fixed to the inner shaft to prevent removal of the superior end plate from the inner shaft, while allowing the superior end plate to rotate relative to the inner shaft. This allows the inner shaft to continue to rotate (and therefore expand) while the superior end plate remained stationary to the superior vertebral body. In some embodiments, superior plates could be swapped with different angles of lordosis or for different endplate engaging features. For example, larger or smaller endplate footprints could be included with the superior end plates, such as, for example, one sized for small or large endplates, or sized for half of an endplate, in the case of a hemi-corpectomy, for example. In some embodiments, the implant includes an internal cage configured to limit rotation of the superior end plate relative to the outer body.

In some embodiments, the geared driver includes a distal pinion gear that is shaped to engage the gear teeth of the inner shaft's thread. The driver may include a handle for providing torsion and/or a shaft that is sized to fit through the port/opening in the outer body. As the gear driver is turned, the pinion teeth engage the threaded gear rack causing it to advance, rotating the inner shaft within the outer body, causing expansion. In some embodiments, the pitch of the thread(s) would dictate the mechanical advantage and therefore ease with which the implant is expanded. For example, the greater the pitch, the greater expansion per rotation of the driver, and vice versa. In some embodiments, the pinion size of the geared driver can be adjusted to provide greater or less torque to the inner shaft, or speed of expansion.

In some embodiments, a locking mechanism is provided between the inner shaft and the outer body to ensure expansion is maintained. In some embodiments, the locking mechanism is a set screw. In some embodiments, the locking mechanism is a ratchet. In some embodiments, the pitch of the thread on the inner shaft is such that the device requires no locking mechanism, but instead the thread pitch won't collapse under its own load. In some embodiments, a detent or positive feature on either the body or the inner shaft could mate with divots or other mating negative features to provide discrete, locked rotational orientations. If a constant, interfering positive feature is used such that any rotational orientation would have enough friction such that the inner shaft wouldn't unthread during loading.

In some embodiments, the expandable implant is a linearly expanding, straight cage.

In some embodiments, the expandable implant is a curved cage that allows expansion along a lordotic or kyphotic curvature. In some embodiments, wherein the expandable implant is a curved cage, the outer body is curved and/or includes curved internal components to accommodate a curved expansion. The curved outer body may be provided with a shape that is anatomically appropriate. In some embodiments, wherein the expandable implant is a linearly expanding, straight cage, the inner shaft is bendable. In particular, the inner shaft includes a spiral cut that matches the thread of the outer body. The spiral cut may include interlocking features that would allow transmission of torque along the axis of the inner shaft. The spiral cut allows the posterior portion of the implant to collapse and the anterior portion of the implant to expand such that the inner shaft could thread/expand along a curvature, rather than along a straight pathway. In some embodiments, wherein the expandable implant is a linearly expanding, straight cage, the implant may include a curved internal cage to give form and structure to the inner shaft. In some embodiments, the curved internal cage has a curve that matches the general curvature of the implant.

In some embodiments, wherein the expandable implant is a curved cage, the implant is a curved, threaded, axially expanding interbody cage. In particular, the novel threaded, toothed central driving shaft provides axial, curved expansion. In some embodiments, the novel threaded, toothed central driving shaft is made by machining. In some embodiments, the novel threaded, toothed central driving shaft is made by 3D printing. In some embodiments, wherein the expandable implant is a curved cage, the implant is configured to expand in a curved fashion, rather than linearly. That is, the implant is configured to expand lordotically, rather than just straight.

In one embodiment, one or all of the components of the spinal implant system are disposable, peel-pack, pre-packed sterile devices used with an implant. One or all of the components of the spinal implant system may be reusable. The spinal implant system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The present disclosure may also be alternatively employed with procedures for treating the lumbar, cervical, thoracic, sacral and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-17, there is illustrated components of a surgical system, such as, for example, a spinal implant system 20.

The components of spinal implant system 20 can be fabricated from biologically acceptable materials suitable for medical applications, including metals, synthetic polymers, ceramics and bone material and/or their composites. For example, the components of spinal implant system 20, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 20 may be employed with surgical procedures, such as, for example, corpectomy and discectomy, which include fusion and/or fixation treatments that employ implants, to restore the mechanical support function of vertebrae.

Spinal implant system 20 includes an expandable interbody implant 22. In some embodiments, implant 22, is a linearly expanding, straight cage and includes an outer body 24 extending along a central longitudinal axis X1 between an end 26 and an opposite end 28. Outer body 24 includes an inner surface 30 defining a bore, such as, for example, a bore 32 and a thread, such as, for example, a female thread 34. Outer body 24 is linear along axis X1 from end 26 to end 28. That is, outer body 24 is straight or non-curved along axis X1 from end 26 to end 28. Outer body 24 includes a port 36 that extends through surface 30 and an opposite outer surface 38 of outer body 24. Port 36 is in communication with bore 32 for providing access to bore 32, as discussed herein. In some embodiments, bore 32 has a uniform diameter along the entire length of bore 32. In some embodiments, bore 32 is coaxial with axis X1 along the entire length of bore 32. In some embodiments, bore 32 and/or port 36 may have various cross section configurations, such as, for example, circular, oval, oblong, triangular, rectangular, square, polygonal, irregular, uniform, non-uniform, variable and/or tapered. In some embodiments, bore 32 may be disposed at alternate orientations, relative to axis X1, such as, for example, transverse and/or other angular orientations such as acute or obtuse, and/or may be offset or staggered. In some embodiments, all or a portion of outer body 24 is made of PEEK. In some embodiments, outer body 24 consists of PEEK.

In some embodiments, implant 22 includes an end plate 40 coupled to end 28. Plate 40 is configured to engage a vertebral body, such as, for example, an end plate of an inferior vertebra, as discussed herein. In some embodiments, plate 40 has a shape that matches or substantially matches the shape of the end plate of the inferior vertebra or an end plate of another vertebra. Plate 40 includes a surface 42 that is coupled directly to a surface of end 28 and a surface 44 opposite surface 42. A distance between surface 42 and surface 44 defines a thickness of plate 40. Plate 40 defines a longitudinal axis X2 that extends perpendicular to axis X1. Plate 40 could be at a fixed angle relative to axis X1 (for example, 10 deg, 15 deg, etc.). End 26 includes an end surface 46 opposite surface 44. In some embodiments, surface 42 extends parallel to surface 44. In some embodiments, surface 46 extends perpendicular to axis X1. In some embodiments, surface 46 extends parallel to axis X2. In some embodiments, surface 46 defines an aperture 48 that is in communication with bore 32. In some embodiments, plate 40 includes a wall 50 defining an opening 52 that is in communication with bore 32. In some embodiments, wall 50 includes a plurality of perforations that extend through the thickness of plate 40 and are in communication with bore 32. In some embodiments, wall 50 has a solid configuration that completely blocks bore 32. In some embodiments, plate 40 is monolithically and/or integrally formed with outer body 24. In some embodiments, plate 40 can be variously connected with outer body 24, such as, for example, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, pivoting/allows pivoting, magnetic connection and/or posts. In some embodiments, all or a portion of plate 40 is made of PEEK. In some embodiments, plate 40 consists of PEEK. In some embodiments, plate 40 could be attached during the procedure per the insitu needs/anatomy/patholog.

In some embodiments, aperture 48 and/or opening 52 has a maximum diameter that is greater than or equal to a maximum diameter of bore 32. In some embodiments, aperture 48 and/or opening 52 has a maximum diameter that is less than or equal to a maximum diameter of bore 32. In some embodiments, aperture 48 and/or opening 52 may have various cross section configurations, such as, for example, circular, oval, oblong, triangular, rectangular, square, polygonal, irregular, uniform, non-uniform, variable and/or tapered. In some embodiments, surface 42 may be disposed at alternate orientations, relative to surface 44, such as, for example, transverse, and/or other angular orientations such as acute or obtuse, and/or may be offset or staggered. That is, in some embodiments, the thickness of plate 40 is uniform along an entire width and/or length of plate 40; and in some embodiments, the thickness of plate is not uniform, such that plate 40 may have be angled or wedge-shaped.

Implant 22 includes an inner shaft 54 extending along a central longitudinal axis X3 between an end 56 and an end 58 opposite end 56. End 58 is positioned in bore 32 such that axis X3 is coaxial with axis X1. Inner shaft 54 comprises an outer surface 60 defining a thread, such as, for example, a male thread 62 that mates with the thread 36 to translate inner shaft 54 relative to outer body 24 in opposite directions along axis X1 in opposite directions, as discussed herein. Thread 62 comprises a series of gear teeth 64 configured to engage a gear of a driver to rotate inner shaft 54 relative to outer body 24 to translate inner shaft 54 relative to outer body 24 in opposite directions along axis X1 in opposite directions, as discussed herein. In some embodiments, teeth 64 are straight cut gear teeth. In some embodiments, teeth 64 include define a bevel gear. In some embodiments, teeth 64 define a helical gear pattern. In some embodiments, surface 60 is smooth and/or even between adjacent roots of thread 62. In some embodiments, all or a portion of inner shaft 54 is made of PEEK. In some embodiments, inner shaft 54 consists of PEEK.

In some embodiments, inner shaft 54 is solid. In some embodiments, inner shaft 54 includes an inner surface 66 opposite surface 60. Surface 66 defines a passageway 68 extending along axis X3. In some embodiments, end 58 includes an opening 70 that is in communication with opening 52 such that material, such as, for example, bone graft material can be inserted through opening 52 and bore 32 and into passageway 68, as discussed herein. In some embodiments, passageway 68 and/or opening 70 may have various cross section configurations, such as, for example, circular, oval, oblong, triangular, rectangular, square, polygonal, irregular, uniform, non-uniform, variable and/or tapered. In some embodiments, passageway 68 may be disposed at alternate orientations, relative to axis X3, such as, for example, coaxial, parallel, transverse and/or other angular orientations such as acute or obtuse, and/or may be offset or staggered.

Figure 5:
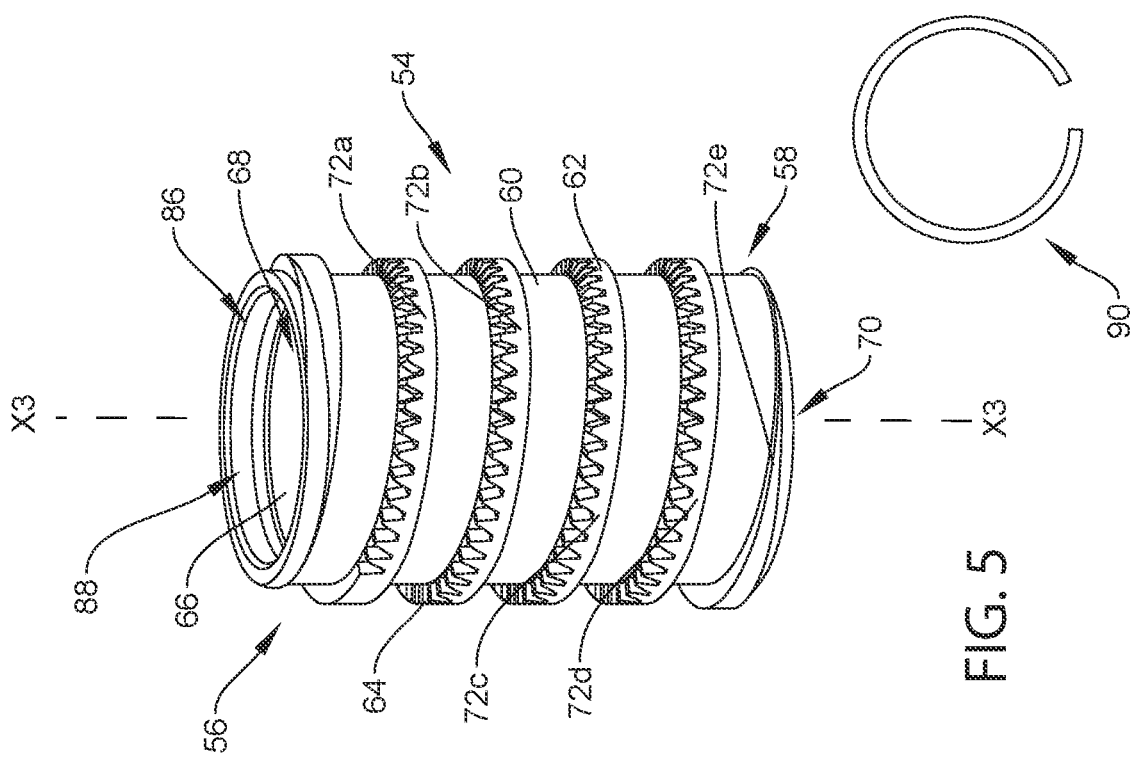
FIG. 5 is a perspective view of a component of the system shown in FIG. 1.
Figure 6:
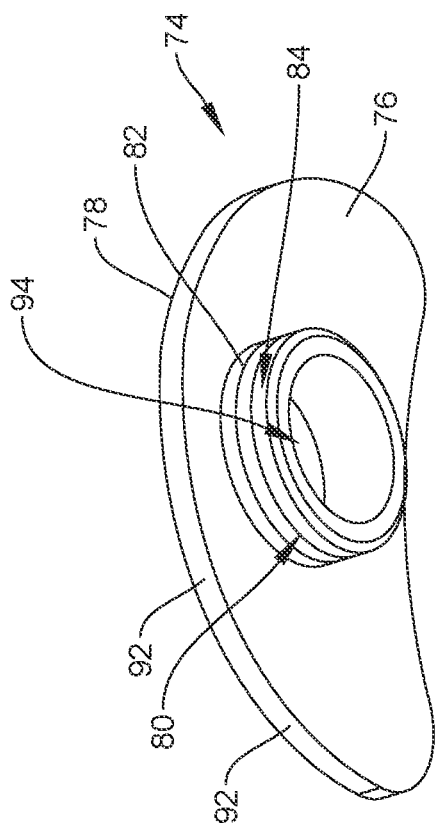
FIG. 6 is a perspective view of a component of the system shown in FIG. 1.
Figure 7:
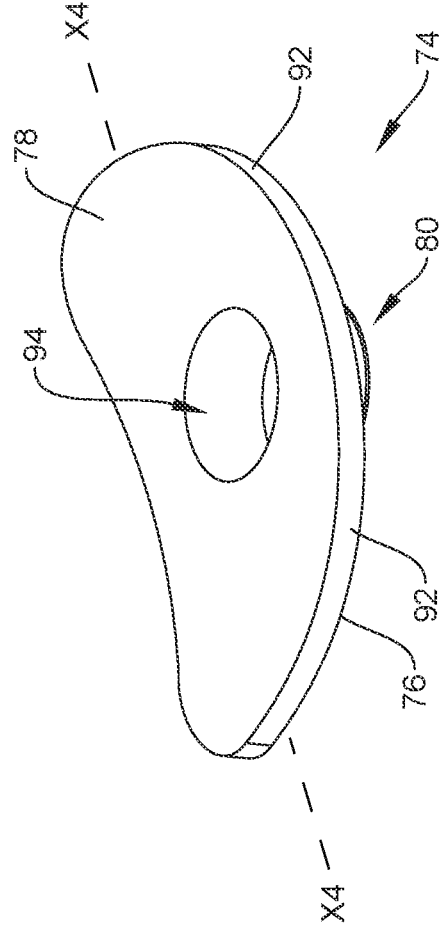
FIG. 7 is a perspective view of a component of the system shown in FIG. 1.
Figure 8:
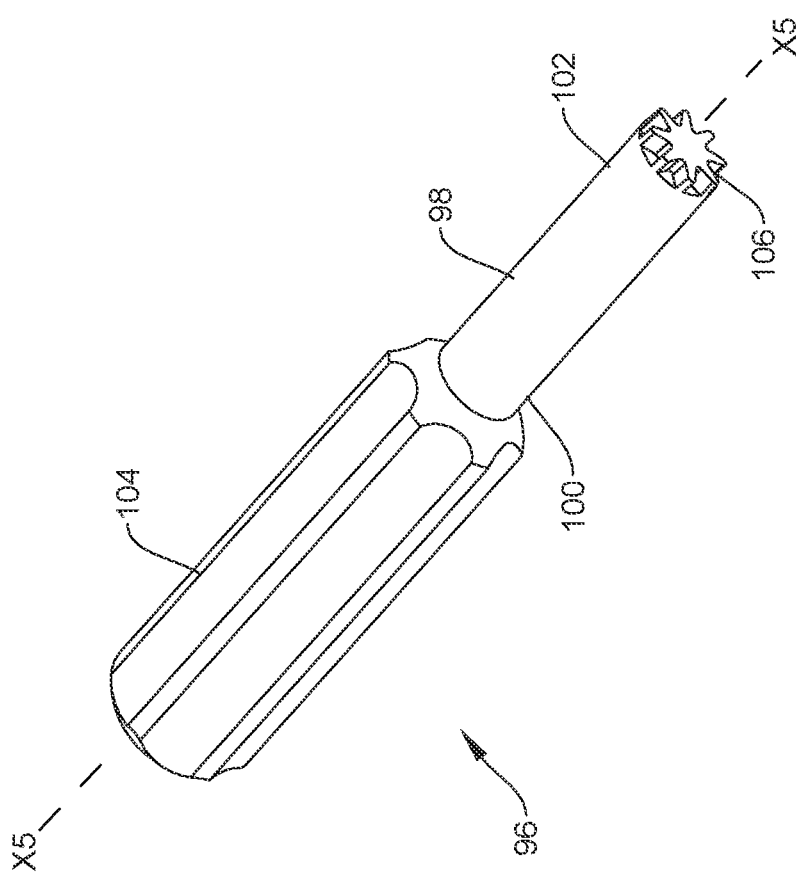
FIG. 8 is a perspective view of a component of the system shown in FIG. 1.

In some embodiments, inner shaft 54 includes a plurality of tiers, such as, for example, tiers 72a, 72b, 72c, 72d, 72e, as best shown in FIG. 5. Tiers 72a, 72b, 72c, 72d, 72e define thread 62. Tiers 72a, 72b, 72c, 72d, 72e are fixed relative to one another as inner shaft 54 translates relative to outer body 24 along axis X1 such that inner shaft 54 does not bend along axis X3 as inner shaft 54 translates relative to outer body 24 along axis X1. That is, because tiers 72a, 72b, 72c, 72d, 72e are fixed relative to one another, inner shaft 54 remains straight as inner shaft 54 translates relative to outer body 24 along axis X1.

Implant 22 includes a superior end plate, such as, for example, a plate 74 coupled to end 56. Plate 74 is configured to engage a vertebral body, such as, for example, an end plate of a superior vertebra, as discussed herein. In some embodiments, plate 74 has a shape that matches or substantially matches the shape of the end plate of the superior vertebra or an end plate of another vertebra. Plate 74 includes a surface 76 and a surface 78 opposite surface 76. A distance between surface 76 and surface 78 defines a thickness of plate 74. Plate 74 defines a longitudinal axis X4. Plate 74 includes a boss 80 extending outwardly from surface 76. Boss 80 includes a wall 82 defining a groove 84. Boss 80 extends through an opening 86 in end 56 for positioning of boss 80 within passageway 68 such that groove 84 is aligned with a groove 88 defined by surface 66. A ring, such as, for example, a snap ring 90 is positioned within grooves 84, 88 to prevent plate 74 from translating relative to inner shaft 54 along axis X3, while allowing plate 74 to rotate relative to inner shaft 54 about axis X3. Face 78 could be angled relative to axis X3. In some embodiments, plate 74 can be variously connected with inner shaft 54, such as, for example, monolithic, integral connection, frictional engagement, threaded engagement, mutual grooves, screws, adhesive, nails, barbs, raised elements, spikes, clips, snaps, friction fittings, compressive fittings, expanding rivets, pivoting/pivotable, staples, fixation plates, key/keyslot, tongue in groove, dovetail, magnetic connection and/or posts. In some embodiments, plate 74 could be attached during the procedure per the insitu needs/anatomy/patholog. In some embodiments, all or a portion of plate 74 is made of PEEK. In some embodiments, plate 74 consists of PEEK. In some embodiments, plate 74 is keyed to the outer body 24.

In some embodiments, plate 74 includes a wall 92 defining an opening 94 that is in communication with passageway 68 when plate 74 is coupled to inner shaft 54 to allow a material, such as, for example, bone graft material to be inserted through opening 94 and into passageway 68. In some embodiments, wall 92 includes a plurality of perforations that extend through the thickness of plate 74 and are in communication with passageway 68. In some embodiments, wall 92 has a solid configuration that completely blocks passageway 68.

System 20 includes a driver 96 comprising a shaft 98 configured to fit through port 36. Shaft 98 extends along a central longitudinal axis X5 between an end 100 and an opposite end 102. A handle 104 is coupled to end 100 and configured to provide torsion. End 102 includes a gear 106 configured to engage teeth 64 such that rotation of shaft 98 relative to outer body 24 and inner shaft 54 about axis X5 rotates inner shaft 54 relative to outer body 24 about axis X1 to translate inner shaft 54 relative to outer body 24 along axis X1. In some embodiments, inner shaft 54 does not bend as inner shaft 54 translates relative to outer body 24 along axis X1 such that axis X4 extends parallel to axis X2 and/or surface 46 as inner shaft 54 translates relative to outer body 24 along axis X1. In some embodiments, inner shaft 54 does not bend as inner shaft 54 translates relative to outer body 24 along axis X1 such that axis X4 extends perpendicular to axis X1 as inner shaft 54 translates relative to outer body 24 along axis X1. In some embodiments, all or a portion of driver 96 is made of PEEK. In some embodiments, driver 96 consists of PEEK.

In assembly, operation and use, spinal implant system 20, similar to the systems and methods described herein, and including implant 22 is employed with a surgical procedure, such as, for example, a lumbar corpectomy for treatment of a spine of a patient including vertebrae. Spinal implant system 20 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of implant 22.

Spinal implant system 20 is employed with a lumbar corpectomy including surgical arthrodesis, such as, for example, fusion to immobilize a joint for treatment of an applicable condition or injury of an affected section of a spinal column and adjacent areas within a body. In some embodiments, implant 22 is configured for insertion within a vertebral space to space apart articular joint surfaces, provide support and maximize stabilization of vertebrae.

In use, to treat the affected section of vertebrae, a medical practitioner obtains access to a surgical site including vertebrae in any appropriate manner, such as through incision and retraction of tissues. In some embodiments, spinal implant system 20 may be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, corpectomy is performed for treating the spine disorder. The diseased and/or damaged portion of vertebrae, and diseased and/or damaged intervertebral discs are removed to create a vertebral space.

A preparation instrument is employed to remove disc tissue, fluids, adjacent tissues and/or bone, and scrape and/or remove tissue from a vertebral surface of a superior vertebra and/or a vertebral surface of an inferior vertebra. Implant 22 may be provided with at least one agent, similar to those described herein, to promote new bone growth and fusion to treat the affected section of vertebrae. The components of spinal implant system 20 may be completely or partially revised, removed or replaced. In some embodiments, implant 22 is employed to stabilize vertebrae as a preassembled device or can be assembled in situ.

Figure 9:
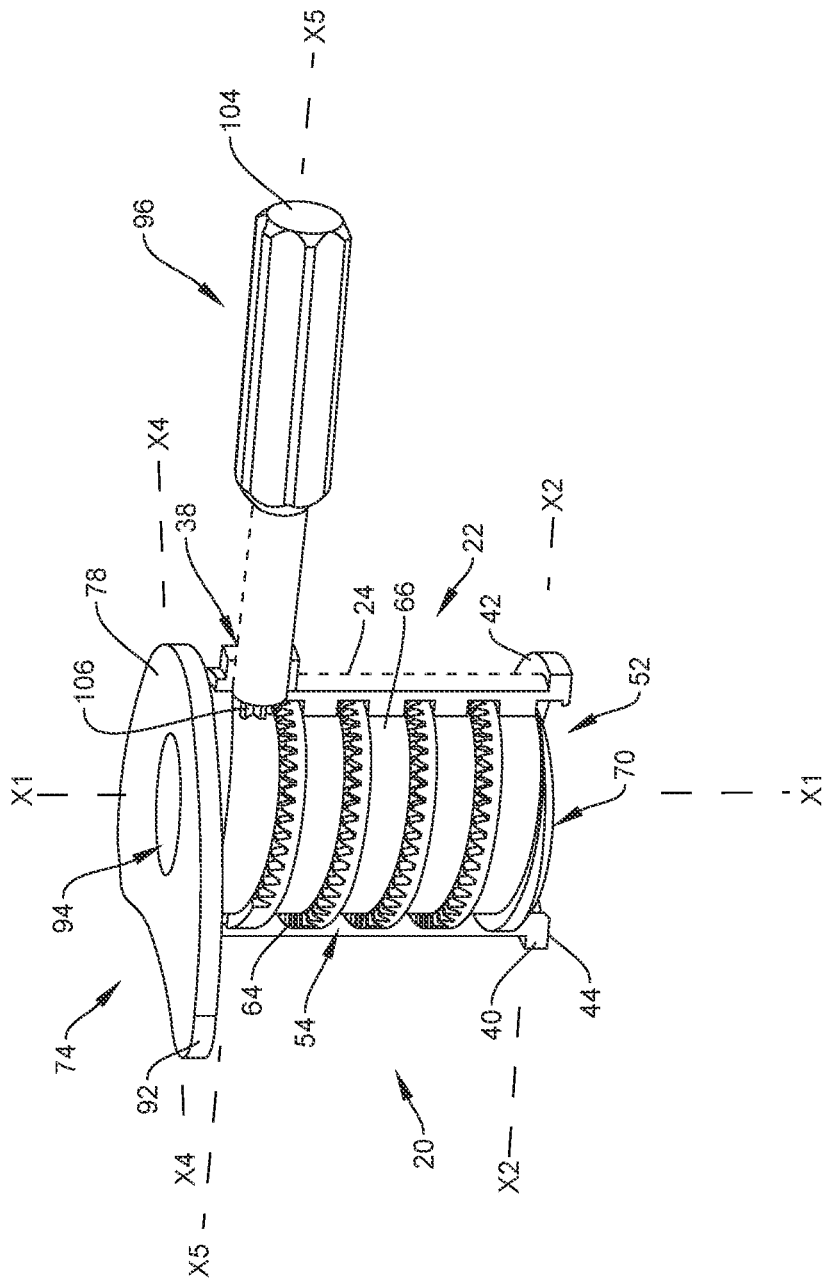
FIG. 9 is a perspective view of components of the system shown in FIG. 1.
Figure 10:
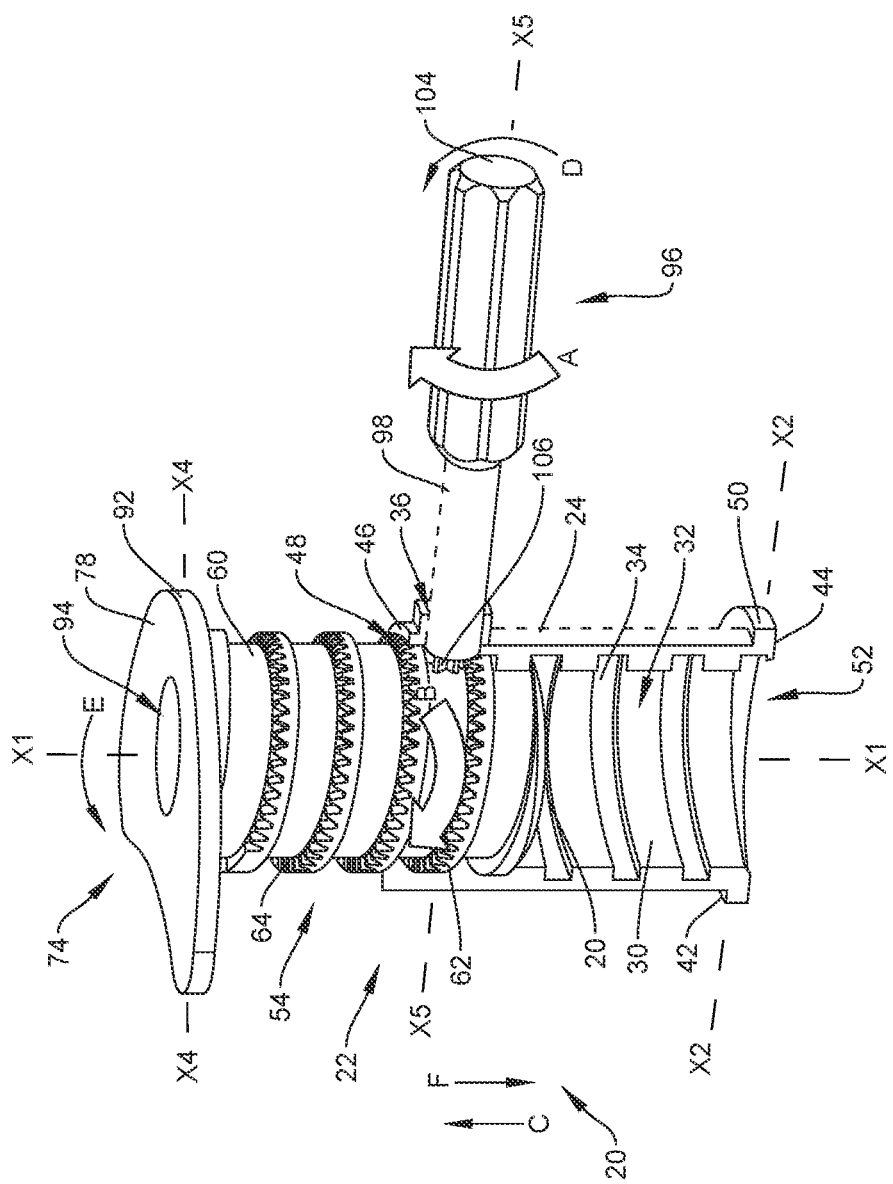
FIG. 10 is a perspective view, in part cross-section, of components of the system shown in FIG. 1.

Implant 22 is inserted into a vertebral space via a posterior approach, with implant 22 in a first configuration, as shown in FIG. 9. When implant 22 is in the first configuration, axis X2 extends parallel to axis X4 and implant 22 has a first height defined by the distance between surface 78 and surface 44. Driver 96 is coupled to implant 22 by inserting shaft 98 through port 36 such that gear 106 engages teeth 64. Shaft 98 is rotated relative to outer body 24 and inner shaft 54 about axis X5 in the direction shown by arrow A in FIG. 10 such that inner shaft 54 rotates relative to outer body 24 in the direction shown by arrow B in FIG. 10 and inner shaft 54 translates relative to outer body 24 in the direction shown by arrow C in FIG. 10 to move implant 22 from the first configuration, shown in FIG. 9, to a second configuration, as shown in FIG. 10. When implant 22 is in the second configuration, axis X2 extends parallel to axis X4 and implant 22 has an increased height defined by the distance between surface 78 and surface 44. That is, the second height is greater than the first height. In some embodiments, plates 74 and 40 are provided at an angle relative to X1 such that when implant 22 is expanded, the vertebral body endplates would be forced apart, but angled relative to each other (with lordosis or kyphosis).

In some embodiments, implant 22 may be moved from the first configuration to the second configuration until surface 78 directly engages an end plate of a superior vertebra and surface 44 directly engages an end plate of an inferior vertebra. In some embodiments, a material, such as, for example, bone graft material is inserted through aperture 52 and into bore 32. In some embodiments, implant 22 includes lateral portals for introducing graft in through the side rather than requiring it to go in from the ends. In some embodiments, implant 22 is loaded with bone graft material from the end on the back table prior to being implanted, and is then loaded with more bone graft material through the lateral portals after implantation. In some embodiments, a material, such as, for example, bone graft material is inserted through aperture 52 and bore 32 and into passageway 68. In some embodiments, the material may move out of passageway 68 and exit implant 22 though opening 94. In some embodiments, a material, such as, for example, bone graft material is inserted through opening 94 and passageway 68 and into bore 32. In some embodiments, the material may move out of bore 32 and exit implant 22 though an opening in inner shaft 54, such as, for example, one or more of the openings discussed herein. In some embodiments, a material, such as, for example, bone graft material is inserted through port 36 and into bore 32. In some embodiments, the material may move out of bore 32 and exit implant 22 though one or more openings in inner shaft 54.

In some embodiments, implant 22 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 20 can be used with screws to enhance fixation. In some embodiments, spinal implant system 20 and any screws and attachments may be coated with an agent, similar to those described herein, for enhanced bony fixation to a treated area. The components of spinal implant system 20 can be made of radiolucent materials such as polymers. Radiomarkers may be included for identification under x-ray, fluoroscopy, CT or other imaging techniques.

In some embodiments, the height of implant 22 may be decreased by coupling driver 96 to implant 22 by inserting shaft 98 through port 36 such that gear 106 engages teeth 64. Shaft 98 is rotated relative to outer body 24 and inner shaft 54 about axis X5 in the direction shown by arrow D in FIG. 10 such that inner shaft 54 rotates relative to outer body 24 in the direction shown by arrow E in FIG. 10 and inner shaft 54 translates relative to outer body 24 in the direction shown by arrow F in FIG. 10 to decrease the height of implant 22.

In some embodiments, the use of microsurgical and image guided technologies may be employed to access, view and repair spinal deterioration or damage, with the aid of spinal implant system 20. Upon completion of the procedure, the non-implanted components, surgical instruments and assemblies of spinal implant system 20 are removed and the incision is closed.

System 30 includes an implant 122, as shown in FIGS. 11-17 that is similar to implant 22. Implant 122 is a curved cage and/or includes curved components in order to facilitate axial, curved expansion. That is, implant 122 is configured to expand lordotically, not just straight. Implant 122 includes an outer body 124 similar to outer body 24. Outer body 124 extends along a central longitudinal axis X6 between an end 126 and an opposite end 128. Outer body 124 includes an inner surface 130 defining a bore, such as, for example, a bore 132 and a thread, such as, for example, a female thread 134. In some embodiments, bore 132 is similar to 132. In some embodiments, thread 134 is similar to thread 34.

Outer body 124 is curved along axis X1 from end 126 to end 128. That is, outer body 124 is curved along axis X6 from end 126 to end 128. In some embodiments, outer body 124 is continuously curved along axis X6. In some embodiments, outer body 124 has a continuous radius of curvature along axis X6. Outer body 124 includes a port 136 that extends through surface 130 and an opposite outer surface 138 of outer body 124. Port 136 is similar to port 36 and is in communication with bore 132 for providing access to bore 132, as discussed herein. In some embodiments, bore 132 is curved along a portion of bore 132 or an entire length of bore 132. In some embodiments, bore 132 includes a central section that is coaxial with axis X6 and upper and lower sections positioned on either side of the central section that are not coaxial with axis X6, due to the curvature of bore 132. In some embodiments, bore 132 and/or port 136 may have various cross section configurations, such as, for example, circular, oval, oblong, triangular, rectangular, square, polygonal, irregular, uniform, non-uniform, variable and/or tapered. In some embodiments, all or a portion of outer body 124 is made of PEEK. In some embodiments, outer body 124 consists of PEEK.

In some embodiments, implant 122 includes an end plate 140 coupled to end 128. Plate 140 is similar to plate 40 and is configured to engage a vertebral body, such as, for example, an end plate of an inferior vertebra, as discussed herein. In some embodiments, plate 140 has a shape that matches or substantially matches the shape of the end plate of the inferior vertebra or an end plate of another vertebra. Plate 140 includes a surface 142 that is coupled directly to a surface of end 128 and a surface 144 opposite surface 142. A distance between surface 142 and surface 144 defines a thickness of plate 140. Plate 140 defines a longitudinal axis X7 that extends perpendicular to axis X6. End 126 includes an end surface 146 opposite surface 144. In some embodiments, surface 142 extends parallel to surface 144. In some embodiments, surface 146 extends at an acute angle relative to axis X6. In some embodiments, surface 146 extends at an acute angle relative to axis X7. In some embodiments, surface 146 defines an aperture 148 that is in communication with bore 132. In some embodiments, plate 140 includes a wall 150 defining an opening similar to opening 52 that is in communication with bore 132. In some embodiments, wall 150 includes a plurality of perforations that extend through the thickness of plate 140 and are in communication with bore 132. In some embodiments, wall 150 has a solid configuration that completely blocks bore 132. In some embodiments, plate 140 is monolithically and/or integrally formed with outer body 124. In some embodiments, plate 140 can be variously connected with outer body 124, such as, for example, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts. In some embodiments, all or a portion of plate 140 is made of PEEK. In some embodiments, plate 140 consists of PEEK.

In some embodiments, aperture 148 has a maximum diameter that is greater than or equal to a maximum diameter of bore 132. In some embodiments, aperture 148 has a maximum diameter that is less than or equal to a maximum diameter of bore 132. In some embodiments, aperture 148 may have various cross section configurations, such as, for example, circular, oval, oblong, triangular, rectangular, square, polygonal, irregular, uniform, non-uniform, variable and/or tapered. In some embodiments, surface 142 may be disposed at alternate orientations, relative to surface 144, such as, for example, transverse, and/or other angular orientations such as acute or obtuse, and/or may be offset or staggered. That is, in some embodiments, the thickness of plate 140 is uniform along an entire width and/or length of plate 140; and in some embodiments, the thickness of plate is not uniform, such that plate 140 may have be angled or wedge-shaped.

Implant 122 includes an inner shaft 154 extending along a central longitudinal axis X8 between an end 56 and an end 158 opposite end 156. End 158 is positioned in bore 132. Inner shaft 154 comprises an outer surface 160 defining a thread, such as, for example, a male thread 162 that mates with the thread 136 to translate inner shaft 154 relative to outer body 124 in opposite directions along axis X6 in opposite directions to expand implant 122 lordotically, as discussed herein. Thread 162 comprises a series of gear teeth 164 configured to engage gear 106 to rotate inner shaft 154 relative to outer body 124 to translate inner shaft 154 relative to outer body 124 in opposite directions along axis X6 in opposite directions to expand implant 122 lordotically, as discussed herein. In some embodiments, surface 160 defines a spiral cut 165 between adjacent roots of thread 162, as discussed herein. In some embodiments, teeth 164 are straight cut gear teeth. In some embodiments, teeth 164 include define a bevel gear. In some embodiments, teeth 164 define a helical gear pattern. In some embodiments, surface 160 is smooth and/or even between adjacent roots of thread 162. In some embodiments, all or a portion of inner shaft 154 is made of PEEK. In some embodiments, inner shaft 54 consists of PEEK.

In some embodiments, inner shaft 154 is solid. In some embodiments, inner shaft 154 includes an inner surface 166 opposite surface 160. Surface 166 defines a passageway 168 extending along axis X8. In some embodiments, end 158 includes an opening 170 that is in communication with an opening in wall 150 such that material, such as, for example, bone graft material can be inserted through the opening in wall 150 and bore 132 and into passageway 168, as discussed herein. In some embodiments, passageway 168 and/or opening 170 may have various cross section configurations, such as, for example, circular, oval, oblong, triangular, rectangular, square, polygonal, irregular, uniform, non-uniform, variable and/or tapered. In some embodiments, passageway 168 may be disposed at alternate orientations, relative to axis X8, such as, for example, parallel, transverse and/or other angular orientations such as acute or obtuse, and/or may be offset or staggered.

Figure 15:
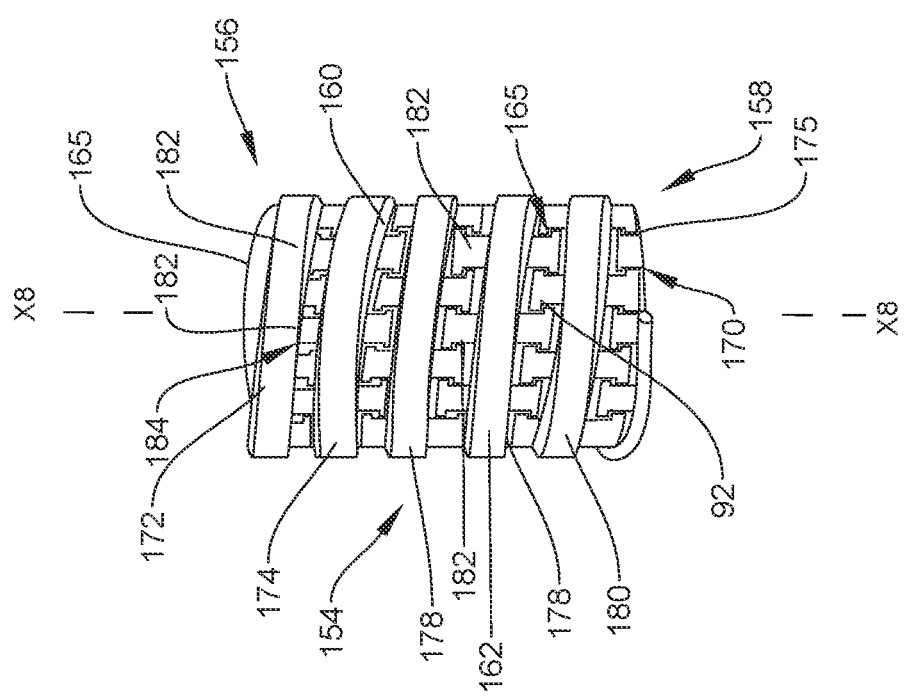
FIG. 15 is a perspective view of a component of the system shown in FIG. 11.
Figure 16:
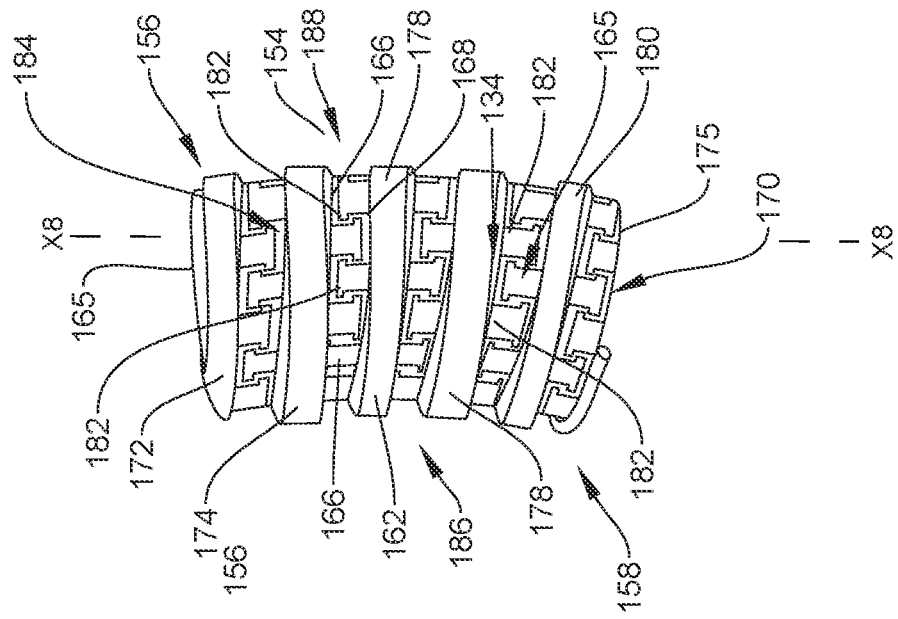
FIG. 16 is a perspective view of a component of the system shown in FIG. 11.
Figure 17:
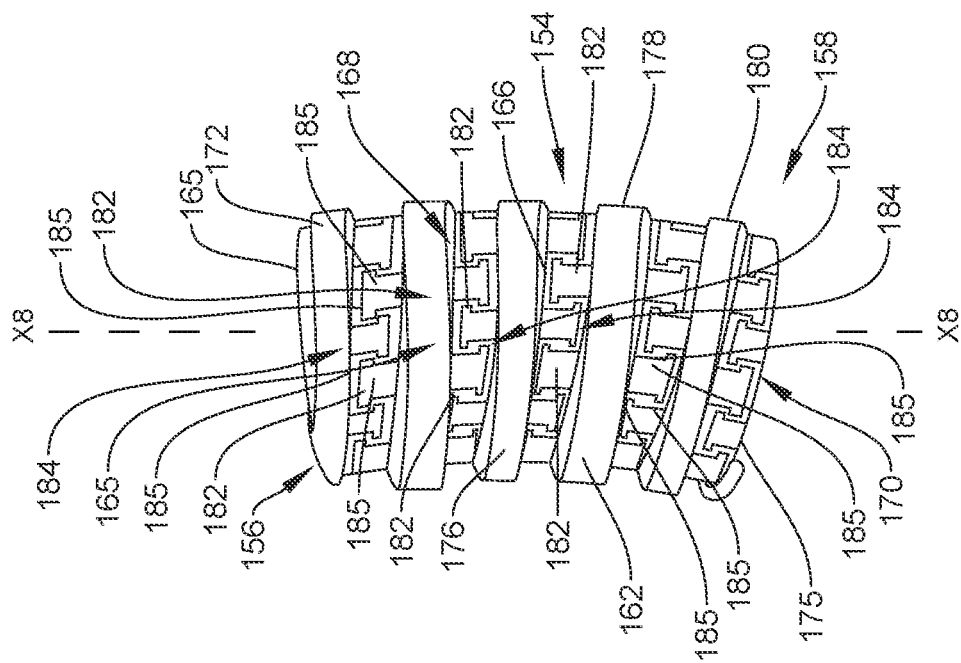
FIG. 17 is a perspective view of a component of the system shown in FIG. 11.

In some embodiments, inner shaft 154 includes a plurality of tiers, such as, for example, tiers 172, 174, 176, 178, 180, as best shown in FIGS. 15-17. Tiers 172, 174, 176, 178, 180 define thread 162. Tiers 172, 174, 176, 178, 180 are movable relative to one another as inner shaft 154 translates relative to outer body 124 along axis X6 such that inner shaft 154 bends along axis X8 as inner shaft 154 translates relative to outer body 124 along axis X6 to expand implant 122 lordotically as inner shaft 154 translates relative to outer body 124 along axis X6. That is, because tiers 172, 174, 176, 178, 180 are movable relative to one another, inner shaft 154 bends as inner shaft 154 translates relative to outer body 124 along axis X6.

Tiers 172, 174, 176, 178, 180 each include spaced apart extensions 182 that define a gap 184 therebetween, as best shown in FIGS. 15-17. Extensions 182 are each movably positioned within one of gaps 184. In some embodiments, extensions 182 each include locking features, such as, for example, flanges 185. Flanges 185 of a respective one of extensions 182 are configured to engage flanges 185 of extensions 182 that define a gap 184 in which the respective one of the extensions 185 is disposed to prevent the respective one of the extensions 185 from moving out of the gap 184 in which the respective one of the extensions 185 is disposed as inner shaft 154 bends along axis X8, as discussed herein.

Movement of extensions 182 within gaps allows inner shaft 154 to move from a first orientation, shown in FIG. 15, in which inner shaft 154 is linear and/or straight, to a second orientation, shown in FIG. 16, in which inner shaft 154 is bent and/or curved. When inner shaft 154 is in the first orientation, an end surface 165 of end 156 extends parallel to an opposite end surface 175 of end 158 and/or passageway 168 is coaxial with axis X8 and/or has a uniform, cylindrical diameter along the entire length of passageway 168. When inner shaft 154 is in the second orientation, surface 165 extends at an acute angle relative to surface 175 and/or at least a portion of a central portion of passageway 168 is offset from axis X8 and/or is bent along the length of passageway 168. In some embodiments, inner shaft 154 conforms to the curvature of outer body 124 when inner shaft 154 is in the second orientation. In some embodiments, a posterior end 186 of inner shaft 154 collapses while an anterior end 188 of inner shaft 154 expands when inner shaft 154 is in the second orientation, as shown in FIG. 16.

Implant 122 includes a superior end plate, such as, for example, a plate 190 coupled to end 156. Plate 190 is configured to engage a vertebral body, such as, for example, an end plate of a superior vertebra, as discussed herein. In some embodiments, plate 190 has a shape that matches or substantially matches the shape of the end plate of the superior vertebra or an end plate of another vertebra. Plate 190 includes a surface 192 and a surface 194 opposite surface 192. A distance between surface 192 and surface 194 defines a thickness of plate 190. Plate 190 defines a longitudinal axis X9. In some embodiments, plate 190 is coupled to inner shaft 154 in the same or similar manner in which plate 74 is coupled to inner shaft 54, as discussed herein. That is, plate 190 is prevented from translating relative to inner shaft 154 along axis X8, while allowing plate 190 to rotate relative to inner shaft 154 about axis X8. In some embodiments, plate 190 can be variously connected with inner shaft 154, such as, for example, monolithic, integral connection, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts. In some embodiments, all or a portion of plate 190 is made of PEEK. In some embodiments, plate 190 consists of PEEK.

Figure 18:
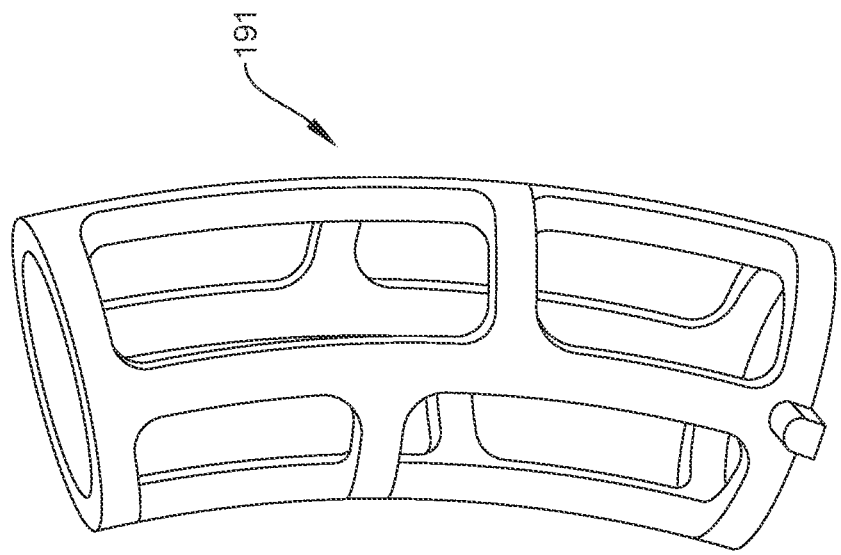
FIG. 18 is a perspective view of a component of the system shown in FIG. 11.
Figure 19:
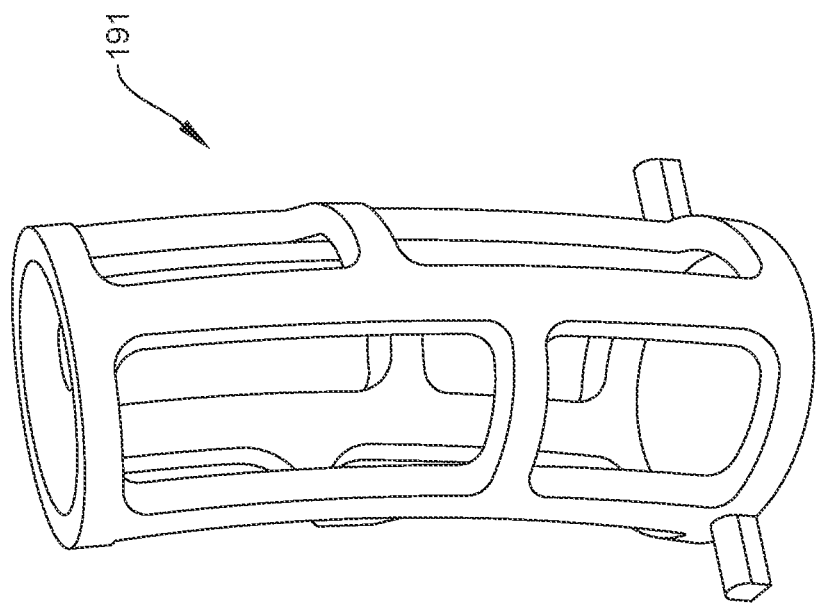
FIG. 19 is a perspective view of a component of the system shown in FIG. 11.

In some embodiments, there is a frame 191 inside of inner shaft 156 that is curved, as shown in FIGS. 18 and 19. In some embodiments, frame 191 has the same radius of curvature as outer body 124 and provides a skeleton for inner shaft 156 to follow and/or provides structure for inner shaft 156. In some embodiments, inner shaft 156 could also prevent rotation of plate 190 from rotating as the device is expanding.

In some embodiments, plate 190 includes a wall 196 defining an opening that is the same or similar to opening 94 and is in communication with passageway 168 when plate 190 is coupled to inner shaft 154 to allow a material, such as, for example, bone graft material to be inserted through the opening in wall 196 and into passageway 168. In some embodiments, wall 196 includes a plurality of perforations that extend through the thickness of plate 190 and are in communication with passageway 168. In some embodiments, wall 196 has a solid configuration that completely blocks passageway 168.

Gear 106 configured to engage teeth 164 such that rotation of shaft 98 relative to outer body 124 and inner shaft 154 about axis X5 rotates inner shaft 154 relative to outer body 124 about axis X6 to translate inner shaft 154 relative to outer body 124 along axis X6. In some embodiments, inner shaft 154 bends as inner shaft 154 translates relative to outer body 124 along axis X6 such that axis X9 extends at an acute angle relative to axis X7 and/or surface 146 as inner shaft 154 translates relative to outer body 124 along axis X6. In some embodiments, inner shaft 154 bends as inner shaft 154 translates relative to outer body 124 along axis X6 such that axis X9 extends at an acute angle relative to axis X6 as inner shaft 154 translates relative to outer body 124 along axis X6. It is noted that as implant 122 expands along a curvature, the relative angle between plates 144 and 192 changes. That is, as implant 122 expands, the angle between plates 144 and 192 increases. Likewise, as implant 122 collapses, the angle between plates 144 and 192 decreases.

In assembly, operation and use, spinal implant system 20, similar to the systems and methods described herein, and including implant 122 is employed with a surgical procedure, such as, for example, a lumbar corpectomy for treatment of a spine of a patient including vertebrae. Spinal implant system 20 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of implant 22.

Spinal implant system 20 is employed with a lumbar corpectomy including surgical arthrodesis, such as, for example, fusion to immobilize a joint for treatment of an applicable condition or injury of an affected section of a spinal column and adjacent areas within a body. In some embodiments, implant 122 is configured for insertion within a vertebral space to space apart articular joint surfaces, provide support and maximize stabilization of vertebrae.

In use, to treat the affected section of vertebrae, a medical practitioner obtains access to a surgical site including vertebrae in any appropriate manner, such as through incision and retraction of tissues. In some embodiments, spinal implant system 20 may be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, corpectomy is performed for treating the spine disorder. The diseased and/or damaged portion of vertebrae, and diseased and/or damaged intervertebral discs are removed to create a vertebral space.

A preparation instrument is employed to remove disc tissue, fluids, adjacent tissues and/or bone, and scrape and/or remove tissue from a vertebral surface of a superior vertebra and/or a vertebral surface of an inferior vertebra. Implant 122 may be provided with at least one agent, similar to those described herein, to promote new bone growth and fusion to treat the affected section of vertebrae. The components of spinal implant system 20 may be completely or partially revised, removed or replaced. In some embodiments, implant 122 is employed to stabilize vertebrae as a pre-assembled device or can be assembled in situ.

Figure 11:
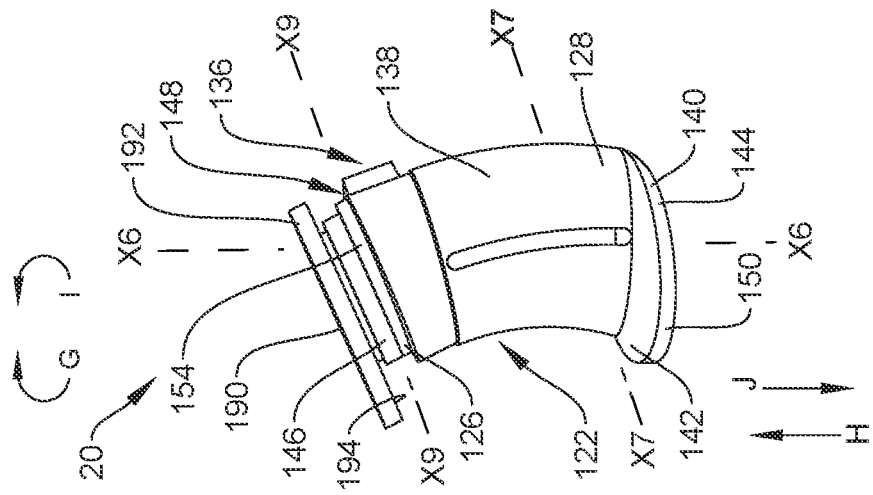
FIG. 11 is a perspective view of components of one embodiment of a spinal implant system in accordance with the principles of the present disclosure.
Figure 12:
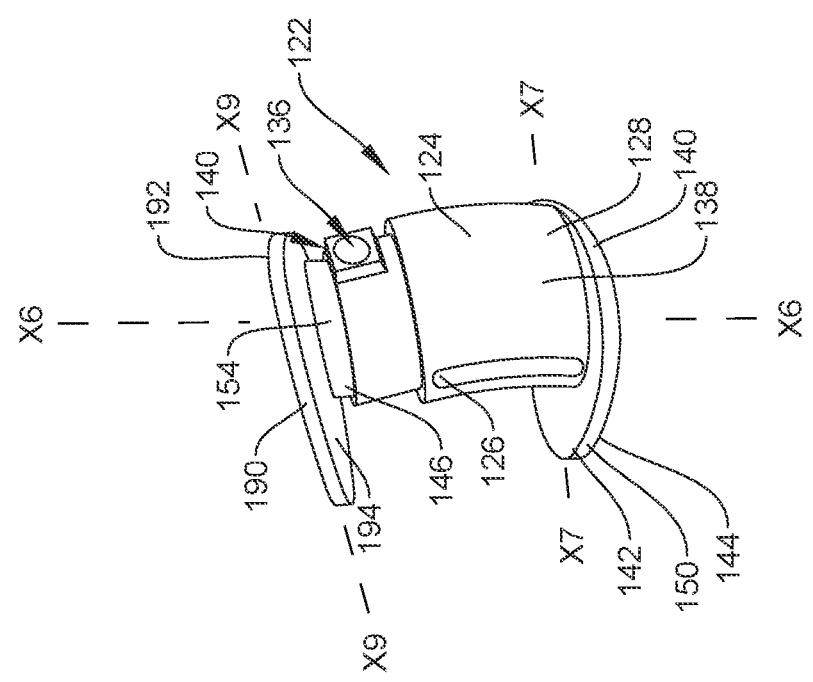
FIG. 12 is a perspective view of components of the system shown in FIG. 11.
Figure 13:
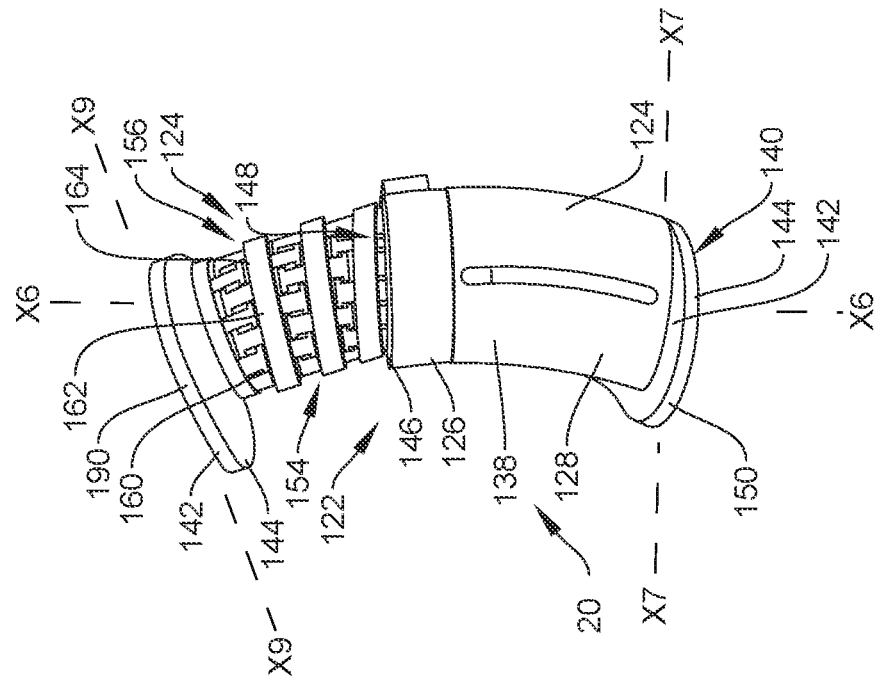
FIG. 13 is a perspective view of components of the system shown in FIG. 11.
Figure 14:
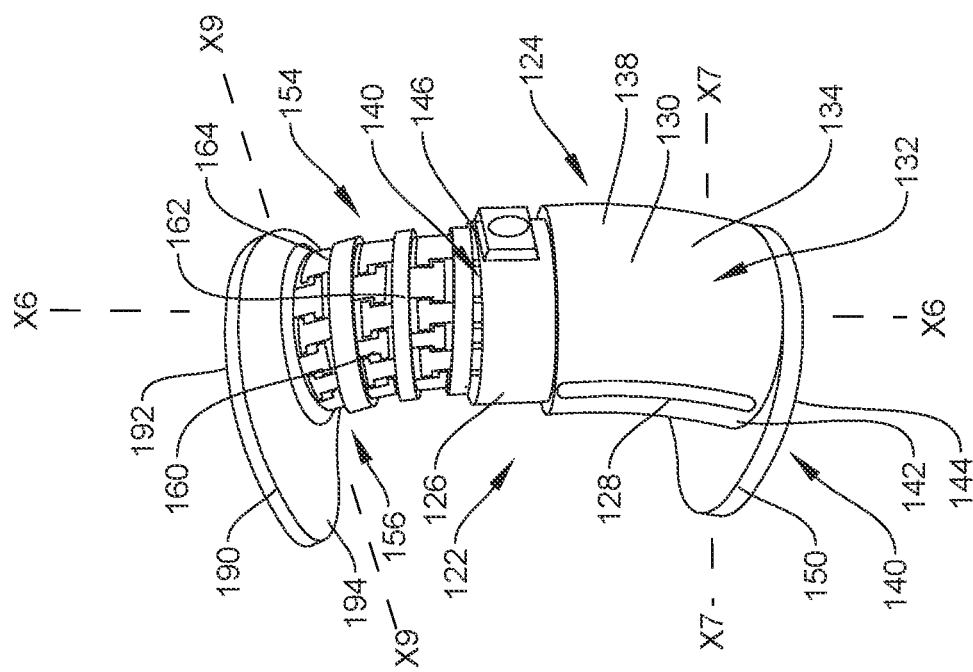
FIG. 14 is a perspective view of components of the system shown in FIG. 11.

Implant 122 is inserted into a vertebral space via a posterior approach, with implant 122 in a first configuration, as shown in FIGS. 11 and 12. When implant 122 is in the first configuration, axis X7 extends at an acute angle relative to axis X9 and implant 122 has a first height defined by the distance between surface 192 and surface 144. Driver 96 is coupled to implant 122 by inserting shaft 98 through port 136 such that gear 106 engages teeth 164. Shaft 98 is rotated relative to outer body 124 and inner shaft 154 about axis X5 in a clockwise direction such that inner shaft 154 rotates relative to outer body 124 in the direction shown by arrow G in FIG. 11 and inner shaft 154 translates relative to outer body 124 in the direction shown by arrow H in FIG. 11 to move implant 122 from the first configuration, shown in FIGS. 11 and 12, to a second configuration, as shown in FIGS. 13 and 14. When implant 122 is in the second configuration, axis X7 extends at an acute angle relative to axis X9 and implant 122 has an increased height defined by the distance between surface 192 and surface 144. That is, the second height is greater than the first height. When implant 122 is in the second configuration, implant 122 is expanded along axis X6 and lordotically.

In some embodiments, implant 122 may be moved from the first configuration to the second configuration until surface 192 directly engages an end plate of a superior vertebra and surface 144 directly engages an end plate of an inferior vertebra. In some embodiments, a material, such as, for example, bone graft material is inserted into implant 122. In some embodiments, a material, such as, for example, bone graft material is inserted through port 136 and into bore 132. In some embodiments, the material may move out of bore 132 and exit implant 122 though an opening in inner shaft 154.

In some embodiments, implant 22 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 20 can be used with screws to enhance fixation. In some embodiments, spinal implant system 20 and any screws and attachments may be coated with an agent, similar to those described herein, for enhanced bony fixation to a treated area. The components of spinal implant system 20 can be made of radiolucent materials such as polymers. Radiomarkers may be included for identification under x-ray, fluoroscopy, CT or other imaging techniques.

In some embodiments, the height of implant 122 and lordosis may be decreased by coupling driver 96 to implant 122 by inserting shaft 98 through port 136 such that gear 106 engages teeth 164. Shaft 98 is rotated relative to outer body 124 and inner shaft 154 about axis X5 in a counterclockwise direction such that inner shaft 154 rotates relative to outer body 124 in the direction shown by arrow I in FIG. 11 and inner shaft 154 translates relative to outer body 124 in the direction shown by arrow J in FIG. 11 to decrease the height of implant 122 and decrease lordosis.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
    an outer body extending along a longitudinal axis between opposite first and second ends, the outer body comprising an inner surface, the inner surface defining a bore and a first thread;
    an inner shaft comprising opposite first and second ends, the second end of the inner shaft being positioned in the bore, the inner shaft comprising a band extending from an outer surface of the inner shaft, the band comprising opposite proximal and distal surfaces, the distal surface extending continuously about inner shaft and defining a second thread that mates with the first thread, the proximal surface defining a series of gear teeth;
    an end plate coupled to the first end of the inner shaft; and
    a driver comprising a gear configured to engage the gear teeth such that rotation of the driver relative to the outer body rotates the inner shaft relative to the outer body to translate the inner shaft relative to the outer body along the longitudinal axis.

2. The spinal implant system recited in claim 1, wherein the longitudinal axis is a first longitudinal axis and the end plate is a first end plate, the outer body comprising a second end plate coupled to the second end of the outer body, the second end plate defining a second longitudinal axis that extends perpendicular to the first longitudinal axis, the first plate defining a third longitudinal axis, the third longitudinal axis being parallel to the second longitudinal axis as the inner shaft translates relative to the outer body along the first longitudinal axis.

3. The spinal implant system recited in claim 1, wherein the longitudinal axis is a first longitudinal axis and the end plate is a first end plate, the outer body comprising a second end plate coupled to the second end of the outer body, the second end plate defining a second longitudinal axis that extends perpendicular to the first longitudinal axis, the first plate defining a third longitudinal axis, the third longitudinal axis extending at an acute angle relative to the second longitudinal axis as the inner shaft translates relative to the outer body along the first longitudinal axis.

4. The spinal implant system recited in claim 1, wherein the outer body is linear along the longitudinal axis from the first end of the outer body to the second end of the outer body.

5. The spinal implant system recited in claim 1, wherein the longitudinal axis is a first longitudinal axis and the end plate is a first end plate, the outer body comprising a second end plate coupled to the second end of the outer body, the second end plate defining a second longitudinal axis that extends perpendicular to the first longitudinal axis, the first end of the outer body comprising an end surface opposite a bottom surface of the second end plate, the end surface defining an opening that is in communication with the bore, the end surface extending parallel to the second longitudinal axis.

6. The spinal implant system recited in claim 1, wherein the outer body is curved along the longitudinal axis between the first end of the outer body to the second end of the outer body.

7. The spinal implant system recited in claim 1, wherein the longitudinal axis is a first longitudinal axis and the end plate is a first end plate, the outer body comprising a second end plate coupled to the second end of the outer body, the second end plate defining a second longitudinal axis that extends perpendicular to the first longitudinal axis, the first end of the outer body comprising an end surface opposite a bottom surface of the second end plate, the end surface defining an opening that is in communication with the bore, the end surface extending at an acute angle relative to the second longitudinal axis.

8. The spinal implant system recited in claim 1, wherein the end plate is a first end plate, the outer body comprising a second end plate coupled to the second end of the outer body, the second end plate comprising a wall defining an aperture that is in communication with the bore.

9. The spinal implant system recited in claim 1, wherein the end plate is a first end plate, the outer body comprising a second end plate coupled to the second end of the outer body, the second end plate comprising a wall defining a plurality of perforations that are each in communication with the bore.

10. The spinal implant system recited in claim 1, wherein the end plate is a first end plate, the outer body comprising a second end plate coupled to the second end of the outer body, the second end plate comprising a wall having a solid configuration that completely blocks the bore.

11. The spinal implant system recited in claim 1, wherein the inner shaft is hollow to allow bone growth.

12. The spinal implant system recited in claim 1, wherein the longitudinal axis is a first longitudinal axis the inner shaft extending along a second longitudinal axis from the first end of the inner shaft to the second end of the inner shaft, the end plate being coupled to the inner shaft such that the end plate is rotatable relative to the inner shaft about the second longitudinal axis and is prevented from translating relative to the inner shaft along the second longitudinal axis.

13. The spinal implant system recited in claim 1, wherein the longitudinal axis is a first longitudinal axis, the inner shaft extending along a second longitudinal axis from the first end of the inner shaft to the second end of the inner shaft, wherein the inner shaft does not bend along the second longitudinal axis as the inner shaft translates relative to the outer body along the first longitudinal axis.

14. The spinal implant system recited in claim 1, wherein the longitudinal axis is a first longitudinal axis, the inner shaft extending along a second longitudinal axis from the first end of the inner shaft to the second end of the inner shaft, wherein the inner shaft bends along the second longitudinal axis as the inner shaft translates relative to the outer body along the first longitudinal axis.

15. The spinal implant system recited in claim 1, wherein the band defines a plurality of tiers, the tiers being fixed relative to one another as the inner shaft translates relative to the outer body along the longitudinal axis.

16. The spinal implant system recited in claim 1, wherein the band defines a plurality of tiers, the tiers moving relative to one another as the inner shaft translates relative to the outer body along the longitudinal axis.

17. The spinal implant system recited in claim 1, wherein the band defines a plurality of tiers, the inner shaft defining a spiral cut between adjacent tiers.

18. The spinal implant system recited in claim 1, wherein the band defines a plurality of tiers, the tiers each including spaced apart extensions that define a gap therebetween, the extensions of the tiers each being movably positioned within the gap of another one of the tiers.

19. A spinal implant system comprising:
- an outer body extending along a first longitudinal axis between opposite first and second ends, the outer body comprising an inner surface, the inner surface defining a bore and a first thread, the outer body being linear along the first longitudinal axis from the first end of the outer body to the second end of the outer body;
- a hollow inner shaft extending along a second longitudinal axis between opposite first and second ends, the second end of the inner shaft being positioned in the bore, the inner shaft comprising a band extending from an outer surface of the inner shaft, the band comprising opposite proximal and distal surfaces, the distal surface extending continuously about inner shaft such that the distal surface extends about a circumference of the inner shaft, the distal surface defining a second thread that mates with the first thread, the proximal surface defining a series of gear teeth, the gear teeth defining gaps between adjacent ones of the gear teeth, the gaps extending into the proximal surface without extending through the distal surface;
- a first end plate coupled to the first end of the inner shaft, the first end plate defining a third longitudinal axis;
- a second end plate coupled to the second end of the outer body, the second end plate defining a fourth longitudinal axis that extends perpendicular to the first longitudinal axis; and
- a driver comprising a gear configured to engage the gear teeth such that rotation of the driver relative to the outer body rotates the inner shaft relative to the outer body to translate the inner shaft relative to the outer body along the first longitudinal axis,
- wherein the fourth longitudinal axis is parallel to the third longitudinal axis as the inner shaft translates relative to the outer body along the first longitudinal axis, and
- wherein the band defines a plurality of tiers, the tiers being fixed relative to one another as the inner shaft translates relative to the outer body along the first longitudinal axis.

20. A spinal implant system comprising:
- an outer body extending along a first longitudinal axis between opposite first and second ends, the outer body comprising an inner surface, the inner surface defining a bore and a first thread, the outer body being linear along the first longitudinal axis from the first end of the outer body to the second end of the outer body;
- a hollow inner shaft extending along a second longitudinal axis between opposite first and second ends, the second end of the inner shaft being positioned in the bore, the inner shaft comprising a band extending from an outer surface of the inner shaft, the band comprising opposite proximal and distal surfaces, the distal surface extending continuously about inner shaft such that the distal surface extends 360 degrees about the inner shaft, the distal surface defining a second thread that mates with the first thread, the proximal surface defining a series of gear teeth, the gear teeth defining V-shaped gaps between adjacent ones of the gear teeth, the gaps extending into the proximal surface without extending through the distal surface, the band comprising an outer surface extending from the proximal surface to the distal surface, the outer surface extending continuously about inner shaft such that the distal surface extends 360 degrees about the inner shaft, the outer surface of the band defining a major diameter of the second thread;
- a first end plate coupled to the first end of the inner shaft, the first end plate defining a third longitudinal axis;
- a second end plate coupled to the second end of the outer body, the second end plate defining a fourth longitudinal axis that extends perpendicular to the first longitudinal axis; and
- a driver comprising a gear configured to engage the gear teeth such that rotation of the driver relative to the outer body rotates the inner shaft relative to the outer body to translate the inner shaft relative to the outer body along the first longitudinal axis,
- wherein the fourth longitudinal axis is parallel to the third longitudinal axis as the inner shaft translates relative to the outer body along the first longitudinal axis, and
- wherein the band defines a plurality of tiers, the tiers being fixed relative to one another as the inner shaft translates relative to the outer body along the first longitudinal axis.

\* \* \* \* \*